US010682057B2

(12) United States Patent
Grodzki et al.

(10) Patent No.: US 10,682,057 B2
(45) Date of Patent: Jun. 16, 2020

(54) REPOSITIONING AN INTERVENTION UNIT ON THE SKIN OF A PATIENT

(71) Applicant: Siemens Healthcare GmbH, Erlangen (DE)

(72) Inventors: David Grodzki, Erlangen (DE); Arne Hengerer, Möhrendorf (DE); Florian Maier, Buckenhof (DE); Rainer Schneider, Hoechstadt (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/445,809

(22) Filed: Jun. 19, 2019

(65) Prior Publication Data

US 2019/0380584 A1 Dec. 19, 2019

(30) Foreign Application Priority Data

Jun. 19, 2018 (DE) .......................... 10 2018 209 885

(51) Int. Cl.
*A61B 5/00* (2006.01)
*A61B 34/20* (2016.01)
(Continued)

(52) U.S. Cl.
CPC .......... *A61B 5/0033* (2013.01); *A61B 8/5238* (2013.01); *A61B 17/3403* (2013.01); *A61B 34/20* (2016.02); *A61B 90/37* (2016.02); *G16H 20/40* (2018.01); *G16H 30/40* (2018.01); *G16H 40/63* (2018.01); *A61B 5/055* (2013.01);
(Continued)

(58) Field of Classification Search
CPC ....... A61B 5/0033; A61B 34/20; A61B 90/37; A61B 17/3403; A61B 8/5238; A61B 8/5207; A61B 6/5229; A61B 10/0233; A61B 8/0841; A61B 34/10; A61B 5/055; A61B 2017/00747; A61B 2034/2065; A61B 2090/061; A61B 2090/062; A61B 2090/366; A61B 2090/3937;
(Continued)

(56) References Cited

U.S. PATENT DOCUMENTS

2012/0226145 A1 9/2012 Chang et al.
2012/0238906 A1* 9/2012 Gilchrest ........... A61B 10/0266
600/567

(Continued)

OTHER PUBLICATIONS

German action dated Dec. 13, 2018 for Application No. 10 2018 209 885.9, and English language translation.

(Continued)

*Primary Examiner* — Amelie R Davis
(74) *Attorney, Agent, or Firm* — Schiff Hardin LLP

(57) ABSTRACT

Techniques are disclosed for preparing a repeat intervention on the skin of a patient. This may include acquiring first image data of an intervention region during a first intervention on the skin of the patient. At least two landmarks may be identified on the skin of the patient on the basis of the acquired first image data. A position of the first intervention is then determined with the aid of the landmarks as reference points. In addition, the position of the first intervention and of the landmarks may be stored in a data memory unit. A position of the second intervention is subsequently localized on the basis of the stored position and of the at least two landmarks.

17 Claims, 4 Drawing Sheets

Figure 1:
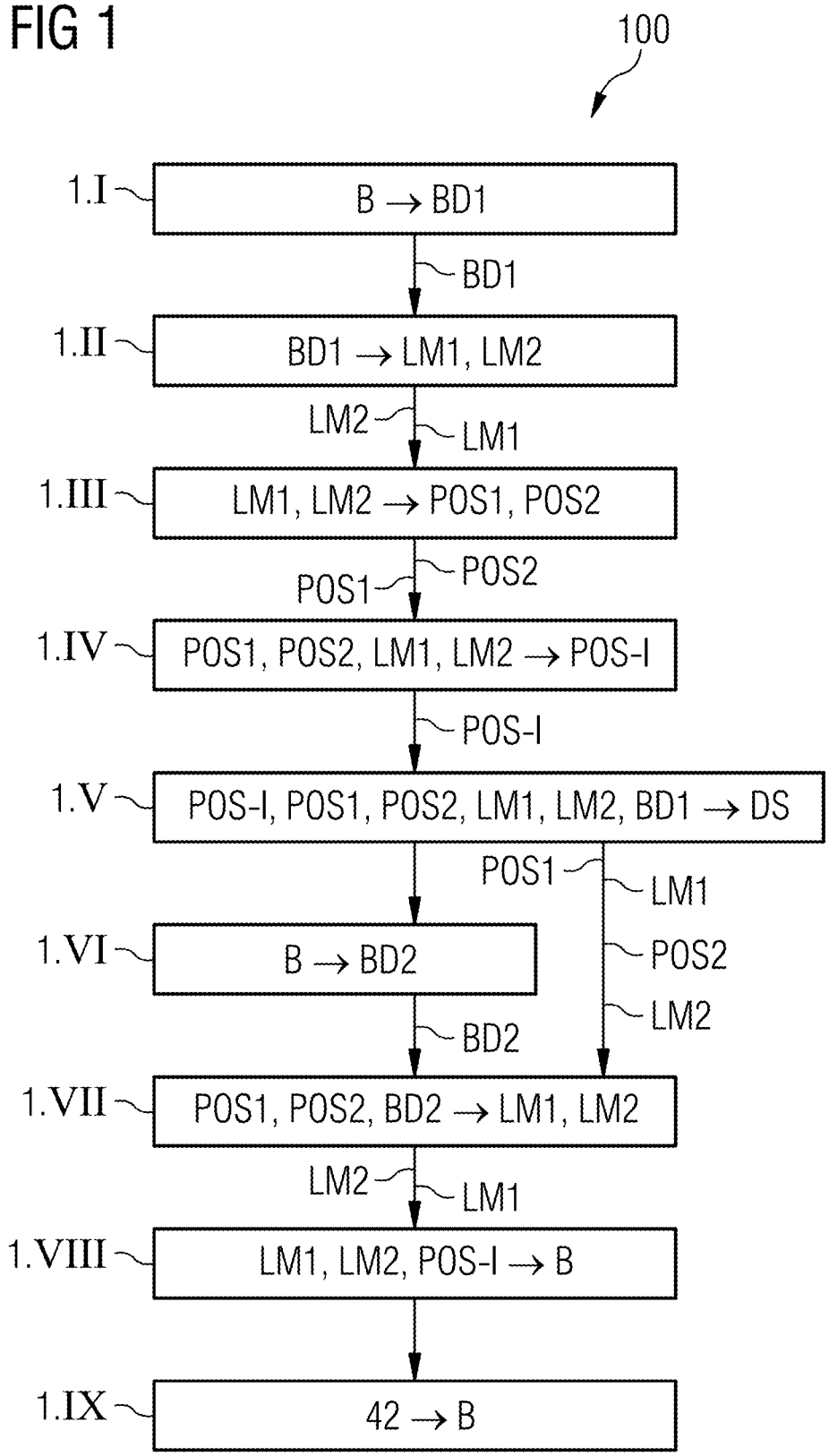

(51) Int. Cl.
- *A61B 90/00* (2016.01)
- *A61B 8/08* (2006.01)
- *A61B 17/34* (2006.01)
- *A61B 34/10* (2016.01)
- *A61B 5/055* (2006.01)
- *A61B 6/00* (2006.01)
- *A61B 10/02* (2006.01)
- *G06T 7/00* (2017.01)
- *G16H 40/63* (2018.01)
- *G16H 20/40* (2018.01)
- *G16H 30/40* (2018.01)
- *A61B 17/00* (2006.01)

(52) U.S. Cl.
CPC ........... *A61B 6/5229* (2013.01); *A61B 8/0841* (2013.01); *A61B 8/5207* (2013.01); *A61B 10/0233* (2013.01); *A61B 34/10* (2016.02); *A61B 90/361* (2016.02); *A61B 2017/00747* (2013.01); *A61B 2034/2065* (2016.02); *A61B 2090/366* (2016.02); *G06T 7/0012* (2013.01)

(58) Field of Classification Search
CPC .... A61B 90/361; G06T 7/0012; G16H 20/40; G16H 30/40; G16H 40/63
See application file for complete search history.

(56) References Cited

U.S. PATENT DOCUMENTS

2014/0364728 A1 12/2014 Hashimoto
2018/0161012 A1 6/2018 Bang et al.

OTHER PUBLICATIONS

German Decision to grant patent dated Mar. 22, 2019, and English language translation.

* cited by examiner

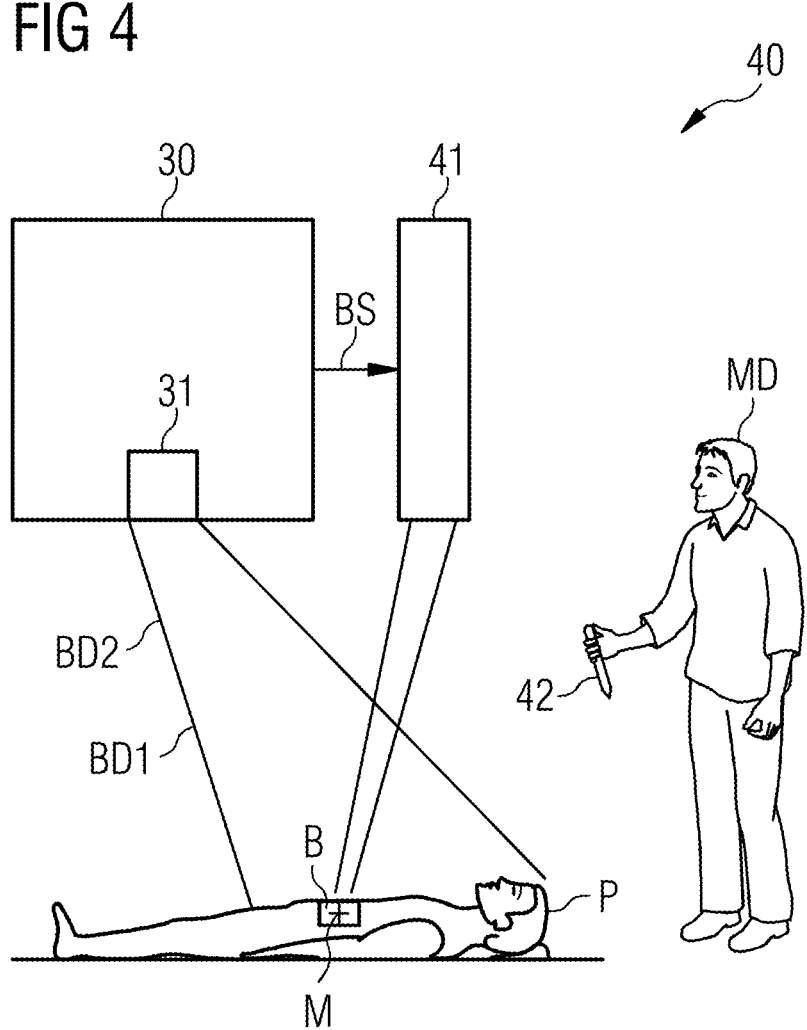

REPOSITIONING AN INTERVENTION UNIT ON THE SKIN OF A PATIENT

CROSS-REFERENCE TO RELATED APPLICATIONS

The present application claims the benefit of the filing date of German patent application no. 10 2018 209 885.9, filed on Jun. 19, 2018, the contents of which are incorporated herein by reference in their entirety.

TECHNICAL FIELD

The present disclosure relates to a method for preparation of a repeat intervention on the skin of a patient, a control facility, and an intervention apparatus.

BACKGROUND

Minimal interventions in the bodies of patients are often required as part of diagnostic and therapeutic methods. These measures may include, for example, targeted percutaneous interventions for taking biopsy samples, radiofrequency (RF) ablations, microwave ablations, laser ablations, etc. The intended aim in such methods is to pinpoint a target region in the body of a patient with maximum precision to enable application of the intervention to the region in question. It is furthermore aimed to choose a puncture site and a puncture angle in such a way that no damage is caused to other surrounding tissue, such as blood vessels, for example. Generally, computed tomography (CT) devices, ultrasound devices, X-ray systems, or MR systems can be used as imaging guidance means to ensure precise positioning.

Often, it is also necessary to repeat the intervention at a later time. For example, the intervention may later be repeated to take biopsy samples from the same body region for checking or monitoring purposes, or to reapply painkillers at a site on the body identified as efficacious. It can frequently be very difficult to achieve a reproducibility of such a procedure when, for example, there are long periods of time between the interventions, the target structure is difficult to visualize, or the intervention is performed by a different clinician or a different institution.

Therefore, to achieve the best possible intervention reproducibility, the puncture site and the puncture angle for a percutaneous intervention must be well documented. Monitoring with the aid of an imaging methods as noted above offers a further means of facilitating the procedure. However, in spite of these measures, it is not possible in many cases to achieve a satisfactory degree of reproducibility. Moreover, some imaging methods require the patient to be exposed to ionizing radiation or require a relatively high specific absorption rate (SAR).

SUMMARY

Therefore, the aspects presented in this disclosure are directed to a method and an apparatus by means of which an improved reproducibility of percutaneous interventions on the skin is made possible. To do so, the aspects described herein utilize a specific method for preparation of a repeat intervention on the skin of a patient, a control facility, and an intervention apparatus, as further discussed below.

In an aspect for preparation of a repeat intervention on the skin of a patient, first image data of an intervention region is acquired during a first intervention on the skin of the patient. The image data can be captured with the aid of an image acquisition unit, such as an imaging camera, for example. At least two "landmarks" are then identified on the skin of the patient on the basis of the acquired first image data. These landmarks are intended to be natural distinctive sub-regions of the surface of a patient, which can be used as reproducible indicators of specific reference positions. Examples of these are the nose, the head, the ears, the costal arch, the pelvic bones, the knees or the feet of the patient, etc.

Preferably, the landmarks are located as close as possible to the puncture site or intervention site so that any error due to bodily movements will be minimized. Furthermore, aspects include determining a position of the first intervention with the aid of the landmarks as reference points and on the basis of the first image data. Because the intervention site is identifiable in the first image data, a position relative to the reference positions of the landmarks can thus be easily determined. The positions of the first intervention and of the landmarks may then be stored in a data memory unit.

Prior to the start of a second intervention, which is intended to take place at the same site as the first intervention, the position of the second intervention is localized (e.g., calculated or otherwise determined) on the basis of the stored position of the first intervention and of the at least two landmarks. In other words, a position of the second intervention on the skin of the patient is determined and unequivocally indicated. Advantageously, a reproducibility of an intervention or of a diagnostic procedure is improved without the duration of the procedure being extended and without ionizing radiation being used to determine the position, thereby avoiding an additional exposure of the patient.

In an aspect, the control facility comprises an image acquisition unit for acquiring first image data of an intervention region during a first intervention on the skin of the patient. The control facility may also comprise an identification unit for identifying at least two landmarks on the skin of the patient on the basis of the acquired first image data. Additionally, aspects include part of the control facility being a position determination unit for determining a position of the first intervention with the aid of the landmarks as reference points. The control facility may further comprise a data memory unit for storing the position of the first intervention and of the landmarks. The control facility may also comprise a localization unit for localizing the position of the second intervention on the basis of the stored position of the first intervention and of the at least two landmarks. The control facility shares the advantages of the method for preparation of a repeat intervention on the skin of a patient.

In an aspect, the intervention apparatus may comprise the control apparatus as well as a display (e.g., a monitor, projector, etc.) for presenting an intervention site on the skin of a patient localized by the control apparatus. The intervention apparatus shares the advantages of the control facility.

Parts of the control facility can be embodied in many cases in the form of software components, and may additionally or alternatively include hardware elements, such as an image acquisition unit and/or one or more hardware processors, for example. This may include, for instance, parts of the identification unit, the position determination unit, and the localization unit. Alternatively, some of these components may be realized in the form of software-assisted hardware, such as field-programmable gate arrays (FPGAs), for example, or the like, which may be particularly useful when there is a requirement for fast calculations. Similarly, the required interfaces may be embodied as software interfaces. This may be, for example, when it is simply a matter of importing data from other software components. The various components of the control facility as discussed herein may, however, also be embodied as hardware-based interfaces that are controlled by suitable software.

A partially software-based implementation has the advantage that computer systems already in use for intervention apparatuses may be easily upgraded by means of a software update to operate in the manner according to the aspects as described herein. In that respect, an object of the present disclosure may be achieved by means of a corresponding computer program product that includes a computer program product that may be loaded directly into a memory facility of such a computer system (e.g., a non-transitory computer-readable memory). Thus, aspects include the computer program product having program sections for the purpose of performing all steps of the method for preparation of a repeat intervention on the skin of a patient when the computer program is executed in the computer system.

As well as the computer program, such a computer program product may include or interact in conjunction with additional constituent parts such as, for instance, a set of documentation and/or additional components. This may include, for example, hardware components, such as hardware keys (dongles, etc.) to allow use of the software.

Aspects include a computer-readable medium (e.g., a non-transitory computer-readable medium) on which the program sections of the computer program may be stored and/or read in and executed by a computer unit, and which may be used for transporting the computer program product to the memory facility of the computer system and/or for storing the same on the computer system. This computer-readable medium may include, for instance, a memory stick, a hard disk, another suitable portable or permanently installed data carrier, etc. For this purpose, the computer unit may comprise, for example, one or more cooperating microprocessors or the like.

In an aspect, the method for preparation of a repeat intervention on the skin of a patient, the localization of the position of the second intervention comprises the steps of: (i) acquiring second image data of the intervention region for the second intervention on the skin of the patient, (ii) identifying the at least two landmarks in the second image data on the basis of the first image data and the positions of the at least two landmarks in the first image data, and (iii) positioning an intervention unit at the position of the first intervention using the at least two landmarks as reference points.

An intervention unit is to be construed in this context as a unit that is in direct contact with the skin of the patient at the time of the intervention at the intervention position. The intervention unit may, for example, comprise a needle by means of which the skin is penetrated at a puncture site, i.e. the intervention site.

Advantageously, a position of the intervention may be determined in the first image data during the first intervention and can be transferred with the aid of the landmarks onto the second image data. In this way, an intervention unit, for example a needle, can be positioned during a second intervention at the same point at which the intervention unit was also positioned during the first intervention.

In another aspect, the method for preparation of a repeat intervention on the skin of a patient and positioning the intervention unit comprises marking the position of the second intervention with the aid of a visualization unit on the basis of the second image data and the identified landmarks as well as of the identified position of the first intervention. Advantageously, a position is indicated to a physician during the preparation of a second intervention on the basis of the current second image data so that an intervention unit can be guided to the same position at which the intervention unit was also positioned during the first intervention.

In another aspect, the method for preparation of a repeat intervention on the skin of a patient includes marking the position of the second intervention and comprises projecting the position of the second intervention onto the skin of a patient. Advantageously, the correct intervention position is indicated directly on the skin of the patient so that navigating to the correct intervention position with an intervention unit is possible in a particularly easy and precise manner.

In another aspect, the method for preparation of a repeat intervention on the skin of a patient includes at least two landmarks, which may be two-dimensional landmarks, for instance. In accordance with such aspects, the skin surface can be modeled approximately as a two-dimensional plane. If two landmarks on said two-dimensional plane are known, then a position of any point on the skin can be unequivocally specified using the two landmarks as reference points. Alternatively, the at least two landmarks may comprise three-dimensional landmarks. Advantageously, reference points can be defined even more precisely in three dimensions in order to determine an exact position for an intervention.

A landmark detection algorithm can be used, for example, for identifying the landmarks. Such a detection algorithm can, for example, be trained by means of a machine learning method with the aid of training data. Advantageously, such a method can be flexibly adapted to fit variable boundary conditions.

In an aspect, the method for preparation of a repeat intervention on the skin of a patient includes localizing the position of the second intervention on the basis of the stored position by localizing a puncture site of the first intervention. Puncture sites can be used, for example, in the treatment of the human body or for diagnostic purposes. For example, an injection, a biopsy, or an ablation can be performed repeatedly at one and the same site. Such a precise procedure can improve the effectiveness of a treatment and/or the precision of a diagnosis.

To determine a position of the first intervention, aspects include specifying a coordinate system in the first image data. In this case, the landmarks are assigned coordinates that can subsequently be easily found during an acquisition of the second image data as a result of the landmarks to be identified there. In this way, the coordinate system generated in the first image data can easily be transferred onto the second image data. A position of the puncture site in the first image data can therefore likewise be unequivocally determined in the second image data.

Additionally, aspects include a surface profile of the skin being determined to determine a position of the first intervention. The surface profile can be recorded, for example, with the aid of a camera or a medical imaging facility, such as am MR system for example. For this purpose, a correction measure known as a HUGE sequence, for example, can be applied. In this, way errors during the relocalization of the intervention site caused by indirect position effects and/or weight changes can be corrected.

In an aspect, the method for preparation of a repeat intervention on the skin, a puncture angle, and/or a puncture depth of a puncture unit used for the first intervention are/is determined. Such a procedure can be performed by means of a moiré phase tracking technique in which moiré markers are placed at terminal points on the puncture unit or the intervention unit. In this way, the puncture angle and/or the puncture depth for the second intervention can also be specified on the basis of the determined puncture angle and/or the determined puncture depth of the first intervention.

The puncture angle and/or the puncture depth for the second intervention can be located, for example, by means of an iterative positioning of an intervention unit. In the process, to prepare for a second intervention, the puncture unit can be guided or tilted until the right angle is found or the right puncture depth is reached. Alternatively, the right puncture angle or the right puncture depth can also be displayed on a visualization unit.

In an aspect, the method for preparation of a repeat intervention on the skin of a patient may be suitable for the thoracic region. In accordance with such aspects, 4D image data of the intervention region is acquired during the first intervention in addition to the acquisition of the first image data. A registration of the 4D image data with the first image data is also performed. A deformation field is determined on the basis of the registered image data and the at least two landmarks. Finally, the position of the second intervention is corrected in the second image data on the basis of the determined deformation field. Motion in the intervention region that would otherwise prevent an exact relocalization of the intervention site (or at least make this more difficult) can be corrected or compensated with the aid of the deformation field.

In an aspect, the method for preparation of a repeat intervention on the skin of a patient, the intervention comprises one of the following procedures: (i) a percutaneous intervention, (ii) a minimally invasive neurointervention, and/or (iii) an intraoperative intervention.

A percutaneous intervention may comprise, for example, making a puncture in the skin in order to inject a therapeutic agent or contrast agent, or to take a sample. A minimally invasive neurointervention may comprise, for example, an imaging operation or a therapeutic procedure in the region of the central nervous system or in the spinal canals. In an intraoperative intervention, an intervention would take place during the operation while the body of the patient is open.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 2:
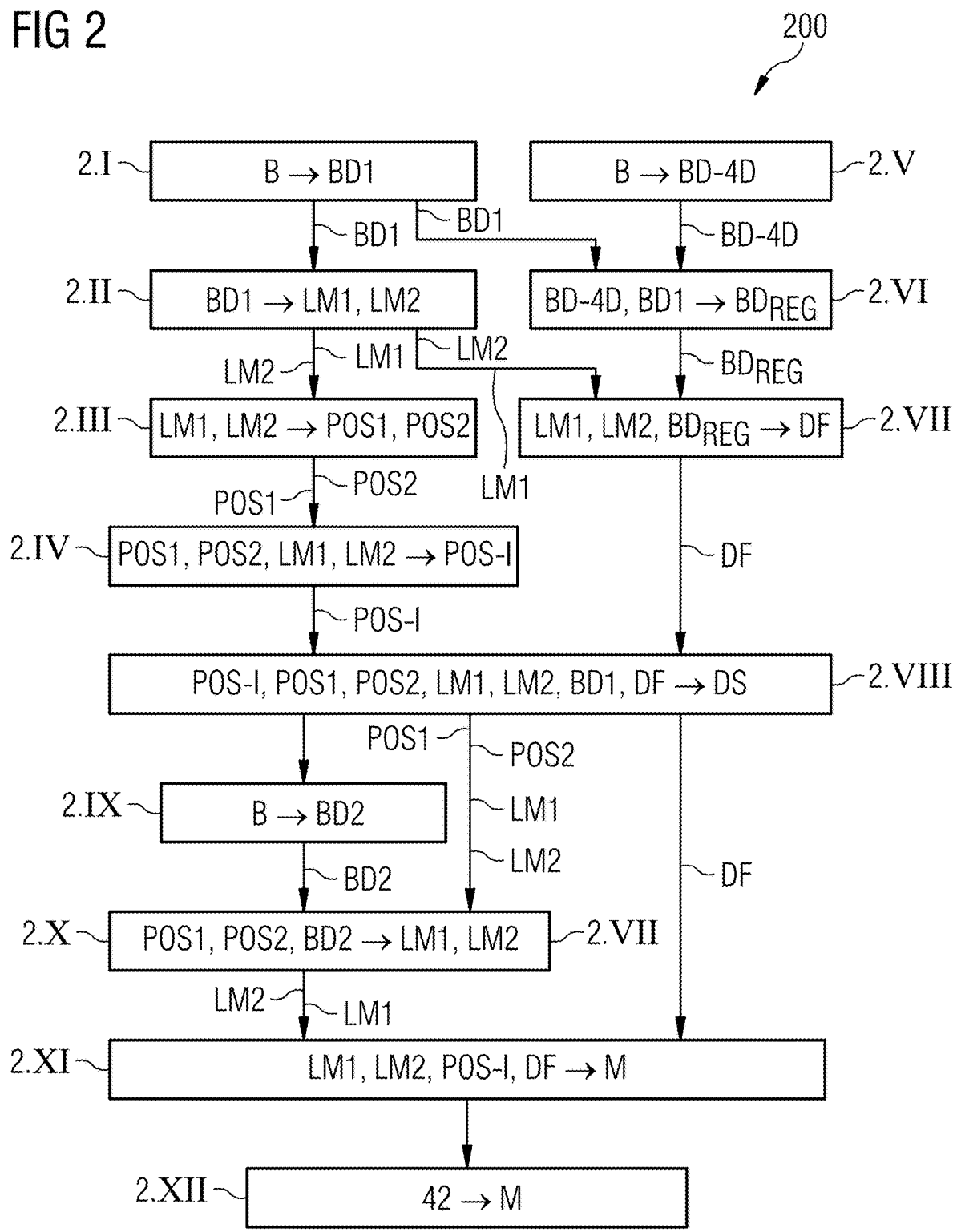
Figure 3:
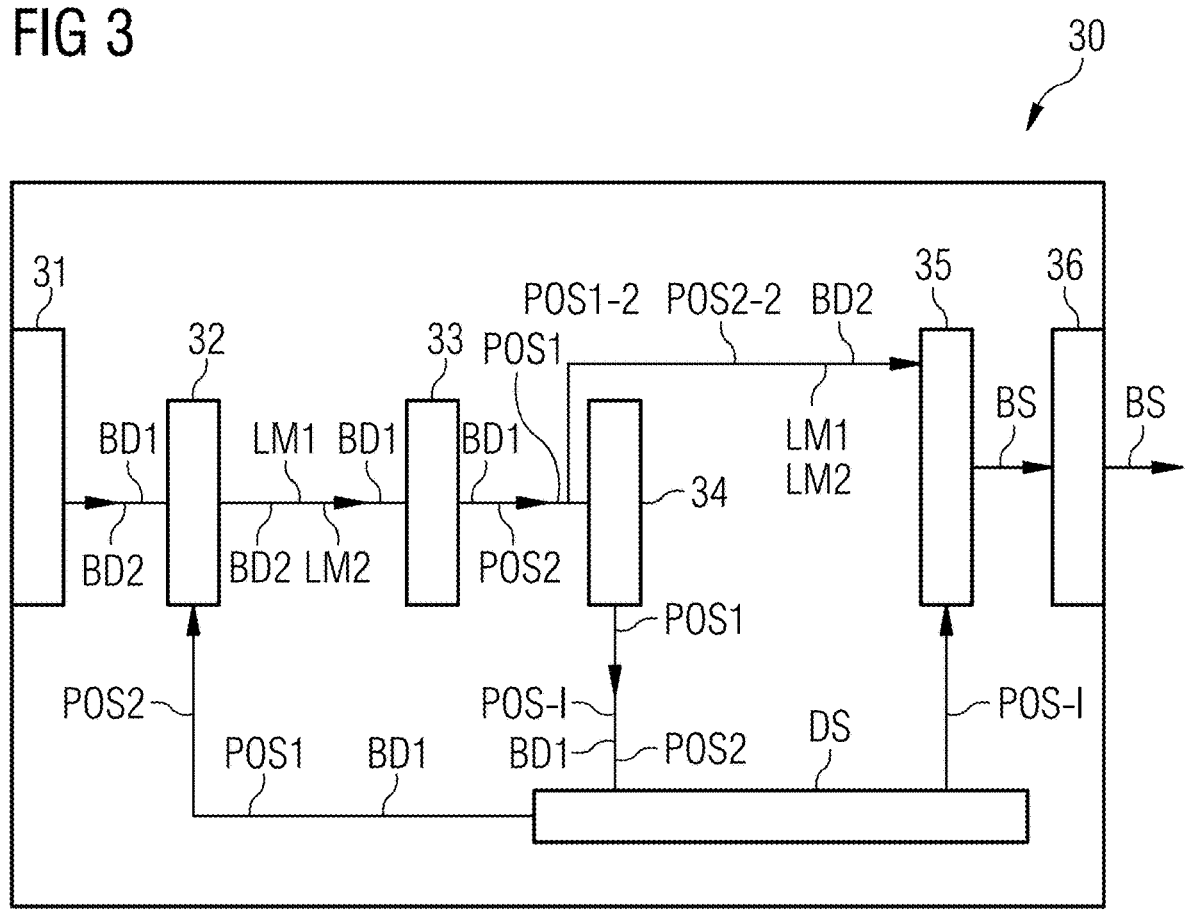

FIG. 1 shows a flowchart illustrating a method for preparation of a repeat intervention on the skin of a patient according to an embodiment, FIG. 2 shows a flowchart illustrating a method for preparation of a repeat intervention on the skin of a patient according to an exemplary embodiment, FIG. 3 shows a schematic representation of a control facility according to an exemplary embodiment, and FIG. 4 shows a schematic representation of an intervention apparatus according to an exemplary embodiment.

The exemplary embodiments of the present disclosure will be described with reference to the accompanying drawings. The drawing in which an element first appears is typically indicated by the leftmost digit(s) in the corresponding reference number.

DETAILED DESCRIPTION

FIG. 1 shows a flowchart illustrating a method for preparation of a repeat intervention on the skin of a patient according to an exemplary embodiment. The method 100 is divided into two parts: a first method part, which is formed by blocks 1.I to 1.V, and a second method part, which comprises blocks 1.VI to 1.IX. In the first method part, a puncture site produced during a first percutaneous intervention is documented (blocks 1.I-1.V). The information ascertained in the process is then used in the second method part (blocks 1.VI-1.IX) to prepare for a further percutaneous intervention, the puncture site produced during the first percutaneous intervention being localized and navigated toward once again with the aid of the cited information.

The method 100 may include the first image data BD1 of an intervention region B on the skin of a patient being acquired (block 1.I) during or after a first percutaneous intervention. The first image data BD1 is recorded with the aid of an imaging camera and shows a puncture site that was produced with the aid of a puncture needle during the first percutaneous intervention. Next, the first image data BD1 is subjected to an image evaluation (block 1.II). This entails conducting a search in the first image data BD1 for landmarks LM1, LM2, which can be used as points of orientation for specifying a coordinate system in the first image data BD1. The method 100 may include positions POS1, POS2 of the landmarks LM1, LM2 then being determined (block 1.III).

The method 100 may further include the position POS-I of the puncture site additionally being determined (block 1.IV) on the basis of the positions POS1, POS2 of the landmarks LM1, LM2 as reference positions. The position POS-I of the puncture site can be determined in this case as a relative position with respect to the positions POS1, POS2 of the landmarks LM1, LM2. Finally, the acquired first image data BD1, the image data of the landmarks LM1, LM2, the positions POS1, POS2 of the landmarks LM1, LM2 and the position POS-I of the puncture site are stored (block 1.V) in a data memory DS. The first method part is thus terminated.

As the second method part, the method 100 may include second image data BD2 of the intervention region B being acquired (block 1.VI) in preparation for a second percutaneous intervention. Next, the two landmarks LM1, LM2 in the second image data BD2 are searched and identified (block 1.VII) in the second image data BD2 with the aid of the image data of the landmarks LM1, LM2 as well as with the knowledge of the positions POS1, POS2 of the landmarks LM1, LM2 in the first image data BD1. Using the known position POS-I of the puncture site that was determined in the first method part, a marker M of the position POS-I of the puncture site is then projected (block 1.VIII) onto the intervention region B. Finally, a needle 42 (see FIG. 4) as interventional tool is placed (block 1.IX) at the position of the marked site in the intervention region B. In doing so, a second percutaneous intervention can be carried out at the same point on the skin at which the first percutaneous intervention was also performed.

FIG. 2 shows a flowchart illustrating a method for preparation of a repeat intervention on the skin of a patient according to an embodiment. Similarly to the method 100 as shown in FIG. 1, the method 200 as shown in FIG. 2 is divided into two parts, the first method part, which is formed by blocks 2.1 to 2.VIII, once again entailing documenting a puncture site produced during a first percutaneous intervention. Next, in the second method part, which comprises blocks 2.IX to 2.XII, the ascertained information is used to prepare a further percutaneous intervention, the puncture site produced during the first percutaneous intervention being localized and navigated toward once again with the aid of the cited information.

In contrast to the method 100 illustrated in FIG. 1, in the method 200 illustrated in FIG. 2, the documenting of the puncture site additionally entails acquiring so-called four-dimensional image data BD-4D, by means of which a deformation field DF can be generated. This deformation field DF helps in compensating for variations in the position of the puncture site relative to the landmarks LM1, LM2 which can be caused by a patient's bodily movement.

In an aspect, the method 200 may begin in the same manner as the method 100, with first image data BD1 of an intervention region B being acquired (block 2.I) during or after a first percutaneous intervention. The first image data BD1 is recorded with the aid of an imaging camera and shows a puncture site that was produced during the first percutaneous intervention. The method 200 may include the first image data BD1 being subjected to an image evaluation (block 2.II). This entails conducting a search in the first image data BD1 for landmarks LM1, LM2 which can be used as points of orientation for specifying a coordinate system in the first image data BD1. The method 200 may further include determining (block 2.III) the positions POS1, POS2 of the landmarks LM1, LM2. The method 200 may include additionally determining (block 2.IV) a position POS-I of the puncture site on the basis of the positions of POS1, POS2 as reference positions. The position POS-I can be determined in this case as a relative position with respect to the positions POS1, POS2 of the landmarks LM1, LM2.

In contrast to the method 100, the method 200 may include additionally acquiring four-dimensional image data BD-4D of the intervention region B (block 2.V). The four-dimensional image data BD-4D comprises time-dependent 3D image data. The method 200 may further include registering (block 2.VI) the four-dimensional image data BD-4D with the acquired first image data BD1. The method 200 may include calculating (block 2.VII) a deformation field DF describing the time-dependent deformation behavior in the intervention region B with the aid of the registered image data BDREG and the identified landmarks LM1, LM2. Finally, the method 200 may include storing (block 2.VIII) the determined position data POS1, POS2 of the landmarks LM1, LM2, as well as the landmarks LM1, LM2 and the position POS-I of the puncture site, plus the first image data BD1 and the deformation fields DF, in a data memory DS. The first method part is thus terminated.

Within the scope of the second method part, the method 200 may include recording (block 2.IX) the second image data BD2 of the intervention region B by means of an imaging camera in preparation for a second percutaneous intervention. Next, the method 200 may include searching for and identifying (block 2.X) the two landmarks LM1, LM2 in the second image data BD2 with the aid of the image data of the landmarks LM1, LM2 and with the knowledge of the positions POS1, POS2 of the landmarks LM1, LM2 in the first image data BD1. The method 200 may include, unlike in the case of the method 100, correcting (block 2.XI) the stored position POS-I of the puncture site on the basis of the stored deformation field DF. Deviations in the position POS-I of the puncture site due to respiratory movements are compensated for in this way. A marker M of the corrected position POS-I of the puncture site is also projected onto the intervention region B. Finally, method 200 may include placing (block 2.XII) a needle 42 (see FIG. 4) as interventional tool at the position of the marked point M. In this way, a second percutaneous intervention can be carried out at the same point on the skin at which the first percutaneous intervention was also performed.

FIG. 3 shows a schematic representation of a control facility according to an exemplary embodiment. As shown in FIG. 3, the control facility 30 comprises an imaging camera 31 with which first and second image data BD1, BD2 of an intervention region B can be recorded during a first intervention and prior to a second intervention on the skin of a patient. Furthermore, the control facility 30 also comprises an identification unit 32 that receives the acquired image data BD1, BD2 from the imaging camera 31 and identifies at least two landmarks LM1, LM2 in the first image data BD1 and the same landmarks LM1, LM2 also in the subsequently acquired second image data BD2. The landmarks LM1, LM2 can be identified with the aid of a landmark detection algorithm, for example. The landmarks LM1, LM2 can for example comprise distinctive parts of the body, such as, for example, the head, the nose, the ears, the costal arch, the pelvic bone, the knees and the feet.

The image data BD1, BD2 containing the identified landmarks LM1, LM2 is then transmitted to a landmark position determination unit 33 that is likewise part of the control facility 30. The landmark position determination unit 33 determines the positions POS1, POS2 of the identified landmarks LM1, LM2 in the first image data BD1 and later also in the second image data BD2. The determined positions POS1, POS2 of the landmarks LM1, LM2 as well as the first image data BD1 are transmitted to a position determination unit 34, which determines a position POS-I of the puncture site as a relative position with respect to the landmarks LM1, LM2 on the basis of the first image data BD1. The first image data BD1 shows, for example, the needle at the puncture site. The position determination unit 34 identifies the puncture site, for example with the aid of a detection algorithm which has been trained by means of a machine learning method, and determines the position POS-I of the identified puncture site as a relative position with respect to the positions POS1, POS2 of the identified landmarks LM1, LM2. The position POS-I of the puncture site, as well as the positions POS1, POS2 of the landmarks LM1, LM2 and the first image data BD1, are additionally transmitted to a data memory unit DS that is likewise part of the control facility 30.

As already mentioned, the imaging camera 31 is also configured to record second image data BD2 of the intervention region B. The acquired image data BD2 is processed by the already mentioned identification unit 32, the identification unit 32 additionally receiving image information BD1 as well as position information POS1, POS2 about the landmarks LM1, LM2 identified in the first image data from the data memory unit DS also to identify the already known landmarks LM1, LM2 in the second image data BD2. In addition, the current positions POS1-2, POS2-2 of the landmarks LM1, LM2 identified in the second image data BD2 are determined by the landmark position determination unit 33.

The determined current position data POS1-2, POS2-2 of the landmarks LM1, LM2 in the second image data BD2, as well as the second image data BD2, are then forwarded to a localization unit 35 that is likewise part of the control facility 30. The localization unit 35 receives the position POS-I of the puncture site determined in the first image data BD1 from the data memory unit, as well as the current positions POS1-2, POS2-2 of the landmarks LM1, LM2 in the second image data BD2 from the position determination unit 33, and determines a position BS of the puncture site on the basis thereof. The position BS of the puncture site is transmitted via an output interface 36 of the control facility 30 to a projection unit 41 (not shown, see FIG. 4).

As noted above, the control facility 30 may include various components implemented as one or more hardware processors and/or additional or alternate software components. Therefore, the various components of the control facility 30 (e.g., the identification unit 32, the position determination unit 33, the position determination unit 34, the localization unit 35, the output interface 36, etc.) may be described and understood as implementing respective hardware circuitry, although the aspects described herein are not limited to exclusive hardware implementations. For example, the identification unit 32, the position determination unit 33, the position determination unit 34, the localization unit 35, the output interface 36, and the data memory unit DS may each be described, respectively, as identification hardware circuitry 32, position determination hardware circuitry 33, position determination hardware circuitry 34, localization hardware circuitry 35, output interface hardware circuitry 36, data memory hardware circuitry DC, etc.

To provide an illustrative example of the overall operation of the control facility aspects as described herein, the control facility 30 may generate one or more control signals (or receive one or more control signals from other portions of the control facility 30) that result in the performance of the various steps discussed herein. For instance, one or more components of the control facility 30 may be interconnected and/or communicatively coupled to one another, and these control signals may control the state and/or operation of these various components. As an example, such control signals may result in the various components associated with the control facility 30 performing the various steps as described herein with reference to FIGS. 1 and 2.

Moreover, the data stored in the data memory DS may be implemented as any suitable type of storage medium (e.g., a non-transitory computer-readable medium) and the data, once acquired, may be stored in any suitable format and in the data memory DS. Moreover, the one or more processors, hardware components, and/or software components associated with the control facility 30 may likewise generate control signals in response to user input, in response to the execution of computer-readable instructions stored in the data memory DS, and/or upon accessing or reading the acquired and stored data. The control signals may thus result in the control facility 30 accessing stored files, executable instructions, etc., which may also be stored in the data memory DS as one or more data files.

The various computing acts performed by the one or more processors, hardware components, and/or software components associated with the control facility 30 may be in response to any combination of user input and/or control signals that are automatically generated in response to the occurrence of certain events. These events may include, as examples, the acquisition of first or second image data of an intervention region during interventions on the skin of the patient, the identification of landmarks on the skin of the patient, the determination of a position of an intervention, the storage of the position of an intervention and landmarks, the localization of the position of the second intervention, etc.

FIG. 4 shows a schematic representation of an intervention apparatus according to an exemplary embodiment. As shown in FIG. 4, an intervention apparatus 40 comprises a control facility 30, which may have any suitable structure such as the structure shown in FIG. 3, for example. As shown in FIG. 4, the intervention apparatus 40 also comprises a projection unit 41. In an aspect, first image data BD1 of a puncture site M in an intervention region B on the skin of a patient P is recorded by means of the camera 31 of the control facility 30 during a first intervention. The first image data BD1 may be processed, for example, in the same manner as described with reference to FIGS. 1-3 as discussed herein.

Additionally, aspects include the intervention apparatus 40 recording second image data BD2 via the camera 31 of the control facility 30 at a point in time shortly before a second intervention by means of a needle. A position BS of the puncture site for the second intervention is determined by the control facility 30 on the basis of the acquired image data BD1, BD2. The determined position data BS in respect of the puncture site is transmitted to the projection unit 41, which, on the basis of the position data BS of the puncture site, projects a marker M of the puncture site onto the body of the patient P in an intervention region B. A physician MD can now position a needle 42 for a second intervention at the marked site and in this way subsequently carry out a second intervention at the same point at which the first intervention was also performed.

Although FIG. 4 illustrates the intervention unit as a needle 42 being administered by the physician MD, aspects include the intervention unit being controlled in an autonomous or semi-autonomous manner. For instance, although not shown in the Figures for purposes of brevity, aspects include the intervention unit (e.g., the needle 42) being mounted within a positioning system that is in communication with the control facility 30. The positioning system may utilize one or more sensors, range detectors, image processors, etc., so as to receive and process data received from the control facility 30 indicating a calculated position and to align and/or insert the intervention unit at the calculated position of the first intervention. Such a positioning system may implement any suitable sensors, including known sensors, feedback devices, and/or processing systems, to implement this functionality.

In conclusion, it is pointed out once again that the embodiments of the methods and apparatuses described in the foregoing are by way of example and not limitation. The various embodiments described herein may be varied by a person skilled in the art without departing from the spirit and scope of the disclosure.

It is also pointed out for the sake of completeness that the use of the indefinite articles "a" or "an" does not exclude the possibility that the features in question may also be present more than once. Similarly, the term "unit" does not rule out the possibility that the same consists of a plurality of components which, where necessary, may also be distributed in space.

Although modifications and changes may be suggested by those skilled in the art, it is the intention of the inventors to embody within the patent warranted hereon all changes and modifications as reasonably and properly come within the scope of their contribution to the art.

The claims described herein and the following description in each case contain additional advantages and developments of the embodiments as described herein. In various aspects, the claims of one claims category can, at the same time, be developed analogously to the claims of a different claims category and the parts of the description pertaining thereto. Furthermore, the various features of different exemplary embodiments and claims may also be combined to create new exemplary embodiments without departing from the spirit and scope of the disclosure.

What is claimed is:

1. A method for determining intervention positions on the skin of a patient, comprising:
   acquiring, via an imaging camera, first image data of an intervention region during a first intervention on the skin of the patient;
   identifying, via one or more processors, at least two landmarks on the skin of the patient using the acquired first image data;
   determining, via the one or more processors, a position of the first intervention using the at least two landmarks as reference points;
   storing, via the one or more processors, the position of the first intervention and positions of the at least two landmarks in a data memory unit; and
   determining, via the one or more processors, a position of a second intervention on the skin of the patient using the stored position of the first intervention and the stored positions of the at least two landmarks.

2. The method as claimed in claim 1, wherein the act of determining the position of the second intervention on the skin of the patient comprises:
   acquiring, via the imaging camera, second image data of the intervention region for the second intervention on the skin of the patient; and
   identifying, via the one or more processors, the at least two landmarks in the second image data using the first image data and the stored positions of the at least two landmarks; and
   positioning a needle at the position of the first intervention for the second intervention using the at least two landmarks as reference points.

3. The method as claimed in claim 2, further comprising:
   marking the position of the second intervention via a projector using the second image data, the identified at least two landmarks, and the position of the first intervention.

4. The method as claimed in claim 3, wherein marking the position of the second intervention comprises projecting the position of the second intervention onto the skin of the patient.

5. The method as claimed in claim 1, wherein the at least two landmarks comprise two-dimensional landmarks.

6. The method as claimed in in claim 1, wherein the at least two landmarks comprise three-dimensional landmarks.

7. The method as claimed in claim 1, wherein a landmark detection algorithm is used to identify the at least two landmarks.

8. The method as claimed in claim 1, wherein the act of determining the position of the second intervention comprises determining, as the position of the second intervention, a puncture site associated with the first intervention.

9. The method as claimed in claim 8, further comprising:
   determining, via moiré phase tracking, at least one of a puncture angle and a puncture depth of a needle assembly used for the first intervention,
   wherein at least one of a puncture angle and a puncture depth for the second intervention is specified using the at least one of the determined puncture angle and the puncture depth used for the first intervention.

10. The method as claimed in claim 9, wherein the at least one of the puncture angle and the puncture depth for the second intervention is determined by means of an iterative positioning of a needle.

11. The method as claimed in claim 1, wherein a coordinate system is specified in the first image data for determining the position of the first intervention.

12. The method as claimed in claim 11, wherein a surface profile of the skin is further used for determining the position of the first intervention.

13. The method as claimed in claim 1, further comprising:
   acquiring 4D image data of the intervention region during the first intervention;
   registering the 4D image data with the first image data;
   determining a deformation field using the at least two landmarks and the registered image data; and
   correcting the position of the second intervention in the second image data using the determined deformation field.

14. The method as claimed in claim 1, wherein the intervention includes at least one of a percutaneous intervention, a minimally invasive neurointervention, and an intraoperative intervention.

15. A control facility, comprising:
   an imaging camera configured to acquire first image data of an intervention region during a first intervention on the skin of a patient;
   identification hardware circuitry configured to identify at least two landmarks on the skin of the patient using the acquired first image data;
   position determination hardware circuitry configured to determine a position of the first intervention with the aid of the at least two landmarks as reference points;
   data memory configured to store the position of the first intervention and positions of the at least two landmarks; and
   localization hardware circuitry configured to determine a position of a second intervention at a same point as the first intervention using the stored position of the first intervention and the stored positions of at least two landmarks.

16. The control facility of claim 15, further comprising:
   a display configured to present an intervention site on the skin of the patient that includes at least one of the determined position of the first intervention or the determined position of the second intervention.

17. A non-transitory computer-readable medium having instructions stored thereon that, when executed by one or more processors, cause the one or more processors to:
   acquire first image data of an intervention region during a first intervention on the skin of a patient;
   identify at least two landmarks on the skin of the patient using the acquired first image data;
   determine a position of the first intervention with the aid of the at least two landmarks as reference points;
   store the position of the first intervention and of the positions of the at least two landmarks; and
   determine a position of the second intervention at a same point as the first intervention using the stored position of the first intervention and the stored positions of at least two landmarks.

* * * * *